(12) United States Patent
Vanderpohl, III

(10) Patent No.: US 10,292,605 B2
(45) Date of Patent: May 21, 2019

(54) BED LOAD CELL BASED PHYSIOLOGICAL SENSING SYSTEMS AND METHODS

(71) Applicant: Hill-Rom Services, Inc., Batesville, IN (US)

(72) Inventor: Irvin J. Vanderpohl, III, Greensburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 798 days.

(21) Appl. No.: 14/069,460

(22) Filed: Nov. 1, 2013

(65) Prior Publication Data

US 2014/0135635 A1 May 15, 2014

Related U.S. Application Data

(60) Provisional application No. 61/726,725, filed on Nov. 15, 2012.

(51) Int. Cl.

| | |
|---|---|
| A61B 5/02 | (2006.01) |
| A61B 5/024 | (2006.01) |
| A61B 5/00 | (2006.01) |
| A61B 5/0205 | (2006.01) |
| A61B 5/11 | (2006.01) |
| G01G 19/44 | (2006.01) |
| A61B 5/08 | (2006.01) |
| A61B 5/113 | (2006.01) |

(52) U.S. Cl.
CPC ............ *A61B 5/024* (2013.01); *A61B 5/0205* (2013.01); *A61B 5/02405* (2013.01); *A61B 5/0816* (2013.01); *A61B 5/1102* (2013.01); *A61B 5/113* (2013.01); *A61B 5/6891* (2013.01); *G01G 19/445* (2013.01); *A61B 5/02* (2013.01); *A61B 5/7203* (2013.01); *A61B 5/725* (2013.01); *A61B 5/7257* (2013.01); *A61B 2562/0252* (2013.01)

(58) Field of Classification Search
CPC ........ A61B 5/02; A61B 5/024; A61B 5/02405
See application file for complete search history.

(56) References Cited

U.S. PATENT DOCUMENTS

| 299,649 A | 6/1884 | Keep et al. |
|---|---|---|
| 1,758,546 A | 5/1930 | Wartmann |
| (Continued) | | |

FOREIGN PATENT DOCUMENTS

| EP | 2 148 179 A1 | 1/2010 |
|---|---|---|
| EP | 2 520 912 A1 | 11/2012 |
| (Continued) | | |

OTHER PUBLICATIONS

Mindmedia, BVP Sensor.*

(Continued)

*Primary Examiner* — Puya Agahi
(74) *Attorney, Agent, or Firm* — Barnes & Thornburg LLP

(57) ABSTRACT

A system for determining a physiological signal of a person supported by a person support apparatus using signals from force transducers is described herein. Force transducers communicate with a controller to transmit signals indicative of weight acting on them. The controller determines blood volume pulse information from the signals received from the force transducers. Heart rate and respiratory rate information is derived from the blood volume pulse information.

26 Claims, 5 Drawing Sheets

(56) References Cited

U.S. PATENT DOCUMENTS

| | | |
|---|---|---|
| 1,969,554 A | 8/1934 | Gloudemans |
| 2,249,645 A | 7/1941 | Applegarth, Sr. |
| 2,260,715 A | 10/1941 | Ketchen |
| 2,425,790 A | 8/1947 | Fletcher |
| 2,430,702 A | 11/1947 | Bohannan |
| 2,644,332 A | 7/1953 | Ulrich |
| 2,735,291 A | 2/1956 | Quinn |
| 2,780,693 A | 2/1957 | McClellan |
| 2,784,395 A | 3/1957 | Gorby |
| 2,818,477 A | 12/1957 | Golhofer |
| 2,819,612 A | 1/1958 | Borgstrom et al. |
| 2,990,899 A | 7/1961 | DeBella |
| 3,096,061 A | 7/1963 | Bertell |
| 3,217,818 A | 11/1965 | Engelsher et al. |
| 3,325,799 A | 6/1967 | Farris |
| 3,338,323 A | 8/1967 | Swersey |
| 3,360,062 A | 12/1967 | Potter |
| 3,418,847 A | 12/1968 | Nantz |
| 3,439,358 A | 4/1969 | Salmons |
| 3,492,865 A | 2/1970 | Johnson |
| 3,504,540 A | 4/1970 | Pradko et al. |
| 3,512,595 A | 5/1970 | Laimins |
| 3,533,095 A | 10/1970 | Collins |
| 3,589,457 A | 6/1971 | Joos |
| 3,656,478 A | 4/1972 | Swersey |
| 3,657,475 A | 4/1972 | Peronneau et al. |
| 3,712,294 A | 1/1973 | Muller |
| 3,722,611 A | 3/1973 | Tirkkonen |
| 3,741,328 A | 6/1973 | Anderson et al. |
| 3,760,794 A | 9/1973 | Bashan |
| 3,766,344 A | 10/1973 | Nevett |
| 3,773,124 A | 11/1973 | Bullivant |
| 3,781,843 A | 12/1973 | Harrison et al. |
| 3,795,284 A | 3/1974 | Mracek et al. |
| 3,796,208 A | 3/1974 | Bloice |
| 3,826,145 A | 7/1974 | McFarland |
| 3,836,900 A | 9/1974 | Mansfield |
| 3,852,736 A | 12/1974 | Cook et al. |
| 3,876,018 A | 4/1975 | Mracek et al. |
| 3,890,958 A | 6/1975 | Fister et al. |
| RE28,754 E | 3/1976 | Cook et al. |
| 3,961,201 A | 6/1976 | Rosenthal |
| 3,961,675 A | 6/1976 | Siegel |
| 3,972,320 A | 8/1976 | Kalman |
| 3,974,491 A | 8/1976 | Sipe |
| 3,988,790 A | 11/1976 | Mracek et al. |
| 3,991,414 A | 11/1976 | Moran |
| 3,991,746 A | 11/1976 | Hanna |
| 4,006,789 A | 2/1977 | Stulz et al. |
| 4,015,677 A | 4/1977 | Silva et al. |
| 4,020,482 A | 4/1977 | Feldl |
| 4,023,633 A | 5/1977 | Swersey et al. |
| 4,066,506 A | 1/1978 | Levy et al. |
| 4,067,005 A | 1/1978 | Levy et al. |
| 4,121,049 A | 10/1978 | Roeber |
| 4,129,189 A | 12/1978 | Maglecic et al. |
| 4,140,998 A | 2/1979 | Bettle |
| 4,175,263 A | 11/1979 | Triplett et al. |
| 4,179,692 A | 12/1979 | Vance |
| 4,195,287 A | 3/1980 | McCoy et al. |
| 4,228,426 A | 10/1980 | Roberts |
| 4,231,030 A | 10/1980 | Weiss |
| 4,242,672 A | 12/1980 | Gault |
| 4,245,651 A | 1/1981 | Frost |
| 4,263,586 A | 4/1981 | Nicholas |
| 4,264,904 A | 4/1981 | McCoy et al. |
| 4,281,730 A | 8/1981 | Swersey et al. |
| 4,282,412 A | 8/1981 | Florin |
| 4,295,133 A | 10/1981 | Vance |
| 4,298,863 A | 11/1981 | Naitus et al. |
| 4,320,766 A | 3/1982 | Alihanka et al. |
| 4,336,533 A | 6/1982 | Wettach |
| 4,337,726 A | 7/1982 | Czekajewski et al. |
| 4,346,771 A | 8/1982 | Persson et al. |
| 4,348,562 A | 9/1982 | Florin |
| 4,363,368 A | 12/1982 | Paddon et al. |
| 4,411,327 A | 10/1983 | Lockery et al. |
| 4,420,052 A | 12/1983 | Hale |
| 4,426,884 A | 1/1984 | Polchaninoff |
| 4,438,823 A | 3/1984 | Hussels et al. |
| 4,474,185 A | 10/1984 | Diamond |
| 4,482,783 A | 11/1984 | Laimins |
| 4,484,043 A | 11/1984 | Musick et al. |
| 4,487,276 A | 12/1984 | Swersey et al. |
| 4,492,281 A | 1/1985 | Van Allen et al. |
| 4,526,043 A | 7/1985 | Boie et al. |
| 4,536,755 A | 8/1985 | Holzgang et al. |
| 4,539,560 A | 9/1985 | Fleck et al. |
| 4,540,057 A | 9/1985 | Freeman |
| 4,550,793 A | 11/1985 | Giles |
| 4,551,882 A | 11/1985 | Swersey et al. |
| 4,558,757 A | 12/1985 | Mori et al. |
| 4,565,910 A | 1/1986 | Musick et al. |
| 4,573,475 A | 3/1986 | Dukes et al. |
| 4,577,185 A | 3/1986 | Andersen |
| 4,583,084 A | 4/1986 | Henderson et al. |
| 4,584,989 A | 4/1986 | Stith |
| 4,595,016 A | 6/1986 | Fertig et al. |
| 4,601,356 A | 7/1986 | Muccillo, Jr. |
| 4,629,015 A | 12/1986 | Fried et al. |
| 4,633,237 A | 12/1986 | Tucknott et al. |
| 4,638,307 A | 1/1987 | Swartout |
| 4,649,759 A | 3/1987 | Lee |
| 4,657,026 A | 4/1987 | Tagg |
| 4,700,180 A | 10/1987 | Vance |
| 4,751,754 A | 6/1988 | Bailey et al. |
| 4,777,944 A | 10/1988 | Green et al. |
| 4,793,428 A | 12/1988 | Swersey |
| 4,796,013 A | 1/1989 | Yasuda et al. |
| 4,803,744 A | 2/1989 | Peck et al. |
| 4,804,052 A | 2/1989 | Griffen |
| 4,805,637 A | 2/1989 | Walthert |
| 4,827,763 A | 5/1989 | Bourland et al. |
| 4,839,512 A | 6/1989 | Speck |
| 4,845,323 A | 7/1989 | Beggs |
| 4,858,622 A | 8/1989 | Osterweil |
| 4,899,840 A | 2/1990 | Boubille |
| 4,907,845 A | 3/1990 | Wood |
| 4,909,338 A | 3/1990 | Vitunic et al. |
| 4,926,951 A | 5/1990 | Carruth et al. |
| 4,934,468 A | 6/1990 | Koerber, Sr. et al. |
| 4,947,152 A | 8/1990 | Hodges |
| 4,947,298 A | 8/1990 | Stephen |
| 4,951,032 A | 8/1990 | Langsam |
| 4,953,244 A | 9/1990 | Koerber, Sr. et al. |
| 4,953,410 A | 9/1990 | Tabota |
| 4,955,947 A | 9/1990 | Hajianpour |
| 4,961,470 A | 10/1990 | Koerber, Sr. |
| 4,967,384 A | 10/1990 | Molinar et al. |
| 4,972,177 A | 11/1990 | Nolan |
| 4,974,692 A | 12/1990 | Carruth et al. |
| 5,003,654 A | 4/1991 | Vrzalik |
| 5,008,654 A | 4/1991 | Callaway |
| 5,010,772 A | 4/1991 | Bourland et al. |
| 5,010,774 A | 4/1991 | Kikao et al. |
| 5,033,563 A | 7/1991 | Brainerd, Jr. et al. |
| 5,044,029 A | 9/1991 | Vrzalik |
| 5,060,174 A | 10/1991 | Gross |
| 5,140,309 A | 8/1992 | Gusakov |
| 5,144,284 A | 9/1992 | Hammett |
| 5,166,679 A | 11/1992 | Vranish et al. |
| 5,170,364 A | 12/1992 | Gross et al. |
| 5,173,977 A | 12/1992 | Carruth et al. |
| 5,183,126 A | 2/1993 | Kellenbach |
| 5,184,112 A | 2/1993 | Gusakov |
| 5,209,126 A | 5/1993 | Grahn |
| 5,232,064 A | 8/1993 | Kroll et al. |
| 5,235,319 A | 8/1993 | Hill et al. |
| 5,253,656 A | 10/1993 | Rincoe et al. |
| 5,268,670 A | 12/1993 | Brasch et al. |
| 5,269,388 A | 12/1993 | Reichow et al. |
| 5,276,432 A | 1/1994 | Travis |

(56) References Cited

U.S. PATENT DOCUMENTS

| | | |
|---|---|---|
| 5,279,010 A | 1/1994 | Ferrand et al. |
| 5,319,817 A | 6/1994 | Hay et al. |
| 5,353,012 A | 10/1994 | Barham et al. |
| 5,393,935 A | 2/1995 | Hasty et al. |
| 5,393,938 A | 2/1995 | Bumbalough |
| 5,410,297 A | 4/1995 | Joseph et al. |
| D361,462 S | 8/1995 | Newham |
| 5,446,391 A | 8/1995 | Aoki et al. |
| 5,448,996 A | 9/1995 | Bellin et al. |
| 5,459,452 A | 10/1995 | DePonte |
| 5,471,198 A | 11/1995 | Newham |
| 5,479,939 A | 1/1996 | Ogino |
| 5,487,196 A | 1/1996 | Wilkinson et al. |
| 5,494,046 A | 2/1996 | Cross |
| 5,519,380 A | 5/1996 | Edwards |
| RE35,301 E | 7/1996 | Reichow |
| 5,554,835 A | 9/1996 | Newham |
| 5,571,142 A | 11/1996 | Brown et al. |
| 5,571,973 A | 11/1996 | Taylot |
| 5,590,650 A | 1/1997 | Genova |
| 5,600,108 A | 2/1997 | Newham |
| 5,602,734 A | 2/1997 | Kithil |
| 5,620,003 A | 4/1997 | Sepponen |
| 5,623,760 A | 4/1997 | Newham |
| 5,633,627 A | 5/1997 | Newham |
| 5,640,145 A | 6/1997 | Newham |
| 5,654,694 A | 8/1997 | Newham |
| 5,664,270 A | 9/1997 | Bell et al. |
| 5,672,849 A | 9/1997 | Foster et al. |
| 5,684,460 A | 11/1997 | Scanlon |
| 5,699,038 A | 12/1997 | Ulrich et al. |
| 5,715,548 A | 2/1998 | Weismiller et al. |
| 5,717,167 A | 2/1998 | Filing et al. |
| 5,747,745 A | 5/1998 | Newman |
| 5,760,688 A | 6/1998 | Kasai |
| 5,767,774 A | 6/1998 | Wright et al. |
| 5,780,781 A | 7/1998 | Berger et al. |
| 5,780,798 A | 7/1998 | Hall-Jackson |
| 5,796,059 A | 8/1998 | Boon |
| 5,801,339 A | 9/1998 | Boult |
| 5,802,479 A | 9/1998 | Kithil et al. |
| 5,802,640 A | 9/1998 | Ferrand et al. |
| 5,808,552 A | 9/1998 | Wiley et al. |
| 5,810,392 A | 9/1998 | Gagon |
| 5,815,864 A | 10/1998 | Sloop |
| 5,823,278 A | 10/1998 | Geringer |
| 5,831,221 A | 11/1998 | Geringer et al. |
| 5,844,488 A | 12/1998 | Musick |
| 5,846,206 A | 12/1998 | Bader |
| 5,859,390 A | 1/1999 | Stafford et al. |
| 5,861,581 A | 1/1999 | Evans et al. |
| 5,861,582 A | 1/1999 | Flanagan et al. |
| 5,869,788 A | 2/1999 | Gordon et al. |
| 5,879,309 A | 3/1999 | Johnson et al. |
| 5,906,016 A | 5/1999 | Ferrand et al. |
| 5,933,083 A | 8/1999 | Sobczynski et al. |
| 5,941,836 A | 8/1999 | Friedman |
| 5,945,914 A | 8/1999 | Holmes et al. |
| 5,957,838 A | 9/1999 | Rantala |
| 5,990,799 A | 11/1999 | Boon et al. |
| 5,999,100 A | 12/1999 | Wright et al. |
| 6,025,782 A | 2/2000 | Newham |
| 6,036,660 A | 3/2000 | Toms |
| 6,047,424 A | 4/2000 | Osborne et al. |
| D424,650 S | 5/2000 | Reichow |
| 6,067,019 A | 5/2000 | Scott |
| 6,075,464 A | 6/2000 | Cloutier et al. |
| 6,078,253 A | 6/2000 | Fowler |
| 6,078,261 A | 6/2000 | Davsko |
| 6,094,762 A | 8/2000 | Viard et al. |
| 6,111,509 A | 8/2000 | Holmes |
| 6,115,860 A | 9/2000 | Vrzalik |
| 6,133,837 A | 10/2000 | Riley |
| 6,147,592 A | 11/2000 | Ulrich et al. |
| 6,166,644 A | 12/2000 | Stroda |
| D436,322 S | 1/2001 | Wajer |
| 6,180,893 B1 | 1/2001 | Salgo |
| 6,204,767 B1 | 3/2001 | Sparks |
| 6,208,249 B1 | 3/2001 | Saito et al. |
| 6,208,250 B1 | 3/2001 | Dixon et al. |
| 6,239,706 B1 | 5/2001 | Yoshiike et al. |
| 6,252,512 B1 | 6/2001 | Riley |
| 6,280,392 B1 | 8/2001 | Yoshimi et al. |
| 6,297,738 B1 | 10/2001 | Newham |
| 6,307,476 B1 | 10/2001 | Smith et al. |
| 6,320,510 B2 | 11/2001 | Menkedick et al. |
| RE37,467 E | 12/2001 | Brasch et al. |
| 6,362,439 B1 | 3/2002 | Reichow |
| 6,362,725 B1 | 3/2002 | Ulrich et al. |
| 6,374,140 B1 | 4/2002 | Rise |
| 6,417,777 B2 | 7/2002 | Fitzgerald et al. |
| 6,438,776 B2 | 8/2002 | Ferrand et al. |
| 6,441,742 B1 | 8/2002 | Lovely et al. |
| 6,450,957 B1 | 9/2002 | Yoshimi et al. |
| 6,502,048 B1 | 12/2002 | Lichtinger et al. |
| 6,544,200 B1 | 4/2003 | Smith et al. |
| 6,546,813 B2 | 4/2003 | Hubbard, Jr. |
| 6,547,743 B2 | 4/2003 | Brydon |
| 6,583,727 B2 | 6/2003 | Nunome |
| 6,636,820 B2 | 10/2003 | Livingston |
| 6,646,556 B1 | 11/2003 | Smith et al. |
| 6,727,445 B2 | 4/2004 | Cullinan et al. |
| 6,784,379 B2 | 8/2004 | Breed et al. |
| 6,784,797 B2 | 8/2004 | Smith et al. |
| 6,791,460 B2 | 9/2004 | Dixon et al. |
| 6,792,342 B2 | 9/2004 | Breed et al. |
| 6,819,254 B2 | 11/2004 | Riley |
| 6,822,571 B2 | 11/2004 | Conway |
| 6,984,207 B1 | 1/2006 | Sullivan et al. |
| 7,077,810 B2 | 7/2006 | Lange et al. |
| 7,100,439 B2 | 9/2006 | Carlucci |
| 7,126,065 B2 | 10/2006 | Petrucelli |
| 7,176,391 B2 | 2/2007 | Metz et al. |
| 7,253,366 B2 | 8/2007 | Bhai |
| 7,296,312 B2 | 11/2007 | Menkedick et al. |
| 7,314,451 B2 | 1/2008 | Halperin et al. |
| 7,335,839 B2 | 2/2008 | Metz et al. |
| 7,437,787 B2 | 10/2008 | Bhai |
| 7,699,784 B2 | 4/2010 | Wan Fong et al. |
| 2001/0001235 A1 | 5/2001 | Menedick et al. |
| 2001/0001237 A1 | 5/2001 | Stroda et al. |
| 2001/0015292 A1 | 8/2001 | Salgo |
| 2002/0067273 A1 | 6/2002 | Jaues et al. |
| 2002/0070867 A1 | 6/2002 | Conway et al. |
| 2002/0080037 A1 | 6/2002 | Dixon et al. |
| 2002/0189924 A1 | 12/2002 | Cullinan et al. |
| 2002/0196148 A1 | 12/2002 | Nunome |
| 2003/0063010 A1 | 4/2003 | Smith et al. |
| 2003/0073936 A1 | 4/2003 | Raisanen |
| 2003/0090383 A1 | 5/2003 | Conway |
| 2003/0114736 A1 | 6/2003 | Reed et al. |
| 2003/0197614 A1 | 10/2003 | Smith et al. |
| 2004/0046668 A1 | 3/2004 | Smith et al. |
| 2004/0087865 A1 | 5/2004 | Kelly |
| 2004/0194220 A1 | 10/2004 | Price et al. |
| 2005/0027416 A1 | 2/2005 | Basir et al. |
| 2006/0028350 A1 | 2/2006 | Bhai |
| 2006/0100534 A1 | 5/2006 | Colombo et al. |
| 2006/0129047 A1 | 6/2006 | Ruotoistenmaki |
| 2007/0118054 A1 | 5/2007 | Pinhas et al. |
| 2007/0149883 A1 | 6/2007 | Yesha |
| 2007/0157385 A1* | 7/2007 | Lemire .................. A61G 7/005 5/600 |
| 2007/0266499 A1 | 11/2007 | O'Keefe et al. |

(56) References Cited

U.S. PATENT DOCUMENTS

| | | | | |
|---|---|---|---|---|
| 2008/0005838 A1* | 1/2008 | Wan Fong | ......... | A61B 5/02444 5/600 |
| 2009/0306487 A1* | 12/2009 | Crowe | ............... | A61B 5/02433 600/322 |
| 2010/0094147 A1* | 4/2010 | Inan | .................... | A61B 5/7207 600/500 |
| 2010/0210921 A1* | 8/2010 | Park | .................... | A61B 5/0205 600/301 |
| 2011/0251493 A1 | 10/2011 | Poh et al. | | |

FOREIGN PATENT DOCUMENTS

| | | | |
|---|---|---|---|
| JP | 200175904 | A1 | 6/2000 |
| JP | 200316915 | A | 11/2000 |
| JP | 2001000401 | A | 1/2001 |
| JP | 2001037821 | A | 2/2001 |
| JP | 2004180804 | A | 7/2004 |
| JP | 2005013259 | A | 1/2005 |
| WO | 94/06348 | A1 | 3/1994 |
| WO | WO 2005/074379 | A2 | 8/2005 |

OTHER PUBLICATIONS

"Is There More to Blood Volume Pulse Than Heart Rate Variability, Respiratory Sinus Arrhythmia, and Cardiorespiratory Synchrony?", Biofeedback, vol. 35, Issue 2, pp. 54-61 (Summer 2007), 8 pages.

European search report from EP 13 19 2273 dated Mar. 24, 2014, 7 pages.

Robin P. Smith, et al., "Pulse transit time: an appraisal of potential clinical applications", Thorax 1999; 54, 452-458.

Poh, Ming-Zher, et al., "MIT Open Access Articles, Non-contact, automated cardiac pulse measurements using video imaging and blind source separation", DSpace@MIT; May 10, 2010/vol. 18. No. 10/Optics Express.

Jean Francois Cardoso, "Dependence, Correlation and Gaussianity in Independent Component Analysis", Journal of Machine Learning Research 4 (2003) 1177-1203.

G.D. Clifford, "Chapter 15-Blind Source Separation: Principal & Independent Component Analysis", HST-5821/6.555J/16.456J; Biomedical Signal and Image Processing; Spring 2008.

* cited by examiner

US 10,292,605 B2

BED LOAD CELL BASED PHYSIOLOGICAL SENSING SYSTEMS AND METHODS

CROSS-REFERENCE TO RELATED APPLICATIONS

The present application claims the benefit, under 35 U.S.C. § 119(e), of U.S. Provisional Application No. 61/726,725, which was filed Nov. 15, 2012, and which is hereby incorporated by reference herein in its entirety.

BACKGROUND

Monitoring physiological parameters of a person supported by a person support apparatus is an ongoing challenge. Space constraints in the patient's vicinity provide opportunities for effective use of technology to monitor the patient without adding to the number of devices in the vicinity of the patient. While several systems and methods exist for sensing physiological signals of a person supported by a person support apparatus, opportunity exists for continued development in this area.

BRIEF SUMMARY

The present disclosure includes one or more of the features recited in the appended claims and/or the following features which, alone or in any combination, may comprise patentable subject matter.

One embodiment of a system may comprise a person support apparatus. At least two force transducers configured to generate signals indicative of forces acting on them may be configured to mount on the person support apparatus. A controller comprising a processor may be configured to receive and process signals from the at least two force transducers to determine blood volume pulse information.

One embodiment of a person support apparatus may comprise a mattress configured to support a person. At least two force transducers may be configured to generate signals indicative of components of weight of a person supported by the mattress acting on the at least two force transducers. A controller comprising a processor may be configured to receive and process signals from the at least two force transducers to determine blood volume pulse information.

One embodiment of a physiological sensing system for use with a person support apparatus may comprise at least two force transducers configured to generate signals in response to weight supported by them. A controller comprising a processor may be configured to receive and process signals from the at least two force transducers to determine blood volume pulse information.

Another embodiment of a system may comprise a person support apparatus, means to generate signals indicative of components of weight acting on the person support apparatus and means to determine blood volume pulse information from the signals indicative of components of weight acting on the person support apparatus.

One embodiment of a method for sensing a physiological signal of a person supported by a person support apparatus may comprise generating signals indicative of components of weight acting on a person support apparatus using at least two force transducers, transmitting the signals to a controller and processing signals indicative of components of weight acting on the person support apparatus to determine blood volume pulse information.

BRIEF DESCRIPTION OF DRAWINGS

The accompanying drawings incorporated in and forming a part of the specification illustrate several aspects of the claimed subject matter and, together with the description, serve to explain the principles of the claimed subject matter. In the drawings:

DETAILED DESCRIPTION OF ILLUSTRATIVE EMBODIMENTS

Figure 1:
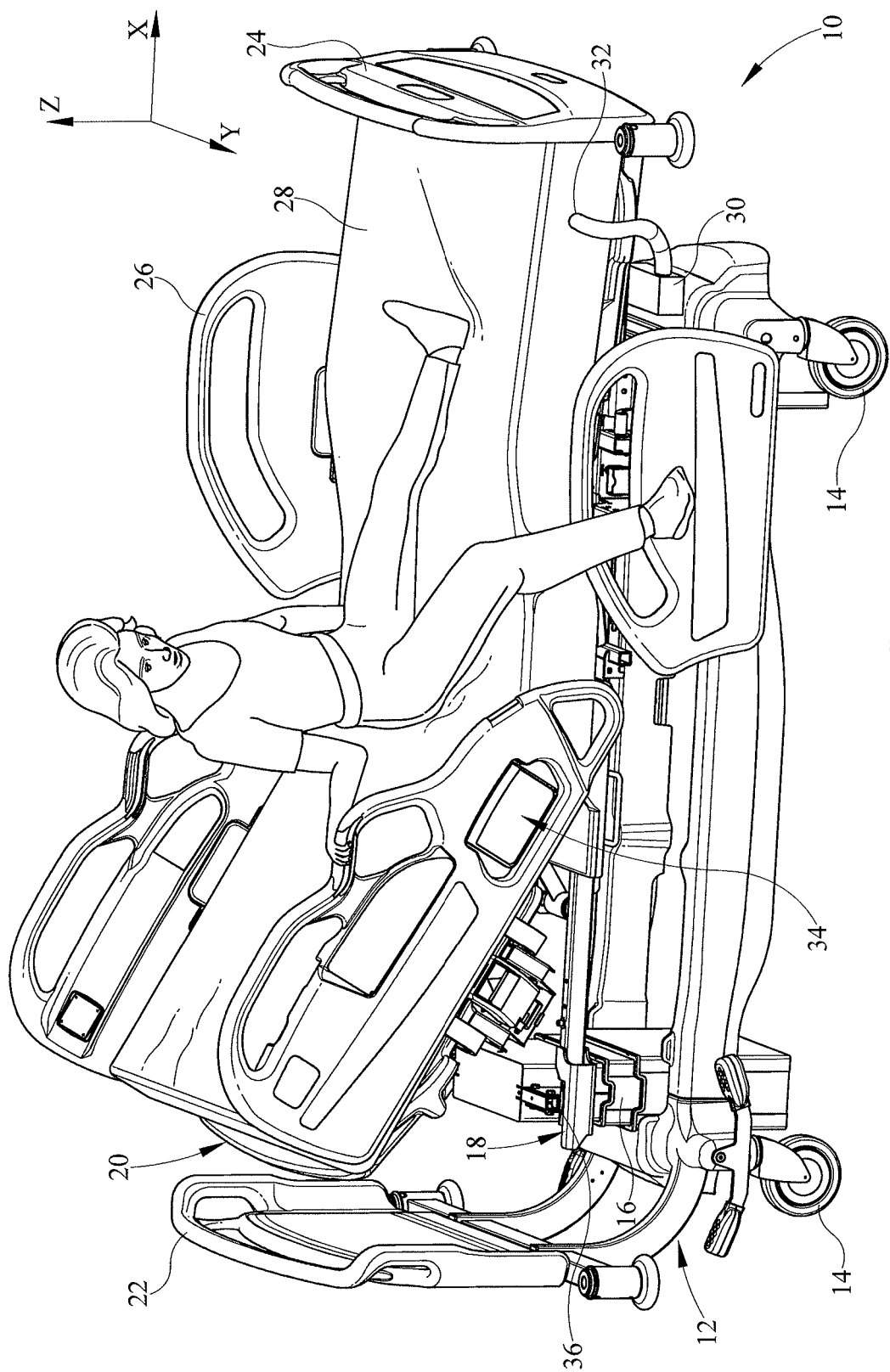
FIG. 1 is a perspective view of a person support apparatus, constructed according to one or more of the principles disclosed herein.

The embodiments of the claimed subject matter and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be briefly mentioned or omitted so as to not unnecessarily obscure the embodiments of the claimed subject matter described. The examples used herein are intended merely to facilitate an understanding of ways in which the claimed subject matter may be practiced and to further enable those of skill in the art to practice the embodiments of the claimed subject matter described herein. Accordingly, the examples and embodiments herein are merely illustrative and should not be construed as limiting the scope of the claimed subject matter, which is defined solely by the appended claims and applicable law. Moreover, it is noted that like reference numerals represent similar parts throughout the several views of the drawings.

It is understood that the subject matter claimed is not limited to the particular methodology, protocols, devices, apparatus, materials, applications, etc., described herein, as these may vary. It is also to be understood that the terminology used herein is used for the purpose of describing particular embodiments only, and is not intended to limit the scope of the claimed subject matter.

Unless defined otherwise, all technical and scientific terms used herein have the same meanings as commonly understood by one of ordinary skill in the art.

The subject matter herein is directed to systems and methods for measuring physiological signals of a person supported by the person support apparatus from signals received from at least two force transducers.

As shown in FIG. 1 a person support apparatus 10 comprises a lower frame 12 supported on wheels 14. In this embodiment a person support apparatus 10 is a bed, while in other embodiments the person support apparatus 10 may be a stretcher or any other furniture. A weigh frame 18 is supported by and configured to variably elevate with respect to lower frame 12 by supports 16 as shown in FIG. 1. At least one deck section 20 is supported on the weigh frame 18. In this embodiment the deck section 20 comprises at least one head support deck section configured to support the upper body of a person, a seat support deck section configured to support the seat section of a person and a foot support deck section configured to support the feet of a person. In another embodiment the deck section 20 may comprise any number of sections. In yet another embodiment the weigh frame 18 may serve the function of the deck section 20 and be comprised of multiple sections.

The person support apparatus also comprises a head board 22 defining the head end, a foot board 24 defining the foot end and side rails 26 defining the lateral extremities of the person support apparatus 10. A mattress 28 is configured to rest upon the deck section 20 of the person support apparatus 10 in this embodiment. In another embodiment, the mattress 28 may be configured to rest upon the weigh frame 18. A fluid supply 30 is configured to supply fluid into the mattress 28 through an inlet 32. In this embodiment the fluid supply 30 is a compressor while in other embodiments the fluid supply 30 may be a blower or a pump. In the embodiment shown in FIG. 1 the fluid supply is mounted on the lower frame 12, while in another embodiment the fluid supply 30 is mounted on the foot board 24. In other embodiments, the fluid supply 30 may be mounted on any other portion of the person support apparatus 10 such as the side rails 26 or the deck section 20. In yet another embodiment the fluid supply 30 may be configured to rest on the floor. In this embodiment the fluid supply 30 is dedicated to the system for supplying dedicated fluid flow in a mattress, while in another embodiment the fluid supply 30 is configured to supply fluid for other uses.

A user interface 34 is mounted on the side rail 26 as shown in FIG. 1 in this embodiment while in another embodiment the user interface 34 is configured to be a hand held pendant. In yet another embodiment the user interface 34 may be at a remote location and configured to communicate with the bed controller wirelessly. The user interface 34 displays system messages and/or allows a caregiver to input control parameters. A co-ordinate system is disclosed in FIG. 1 to assist in description of relative positions and motions. As shown, X axis is configured to pass through the middle of the width of the person support apparatus. Axis Y is orthogonal to the X axis such that the X-Y plane is substantially parallel to the weigh frame. Axis Z is orthogonal to the X-Y plane.

A number of force transducers which are load cells 36 in this embodiment are positioned between the weigh frame 18 and the lower frame 12 in this embodiment. In other embodiments the load cells 36 may be positioned between the deck section 20 and the weigh frame 18. In other embodiments the weigh frame may be mounted anywhere on the person support apparatus 10 and/or the mattress 12. In yet another embodiment the load cells 36 are mounted to a sheet positioned on top of the person support apparatus 10 and/or the mattress 12. Load cells 36 are configured to generate a signal indicative of the force experienced by them and in this embodiment the load cell 36 is configured to generate an electrical signal, while in other embodiments the load cells 36 may generate any type of signal including but not limited to optical signals. In other embodiments any other type of force transducer may be used instead and/or in combination with load cells.

Conventional structures and devices may be provided to adjustably position deck section 20, and such conventional structures and devices may include linkages, drives and other movement members and devices coupled between the weigh frame 18 and the lower frame 12 and/or between the weigh frame 18 and the deck section 20. Control of the position of the deck section 20 and mattress 28 relative to the lower frame 12 is provided in one embodiment by user interface 34, mattress position control panel (not shown) and/or a number of mattress positioning pedals (not shown).

Embodiments of person support systems are found in patents U.S. Pat. Nos. 7,296,312, 6,047,424, 7,176,391, 7,335,839, 7,437,787, 7,253,366 and patent application publication US2007/0266499, all of which are incorporated by reference herein.

Figure 2:
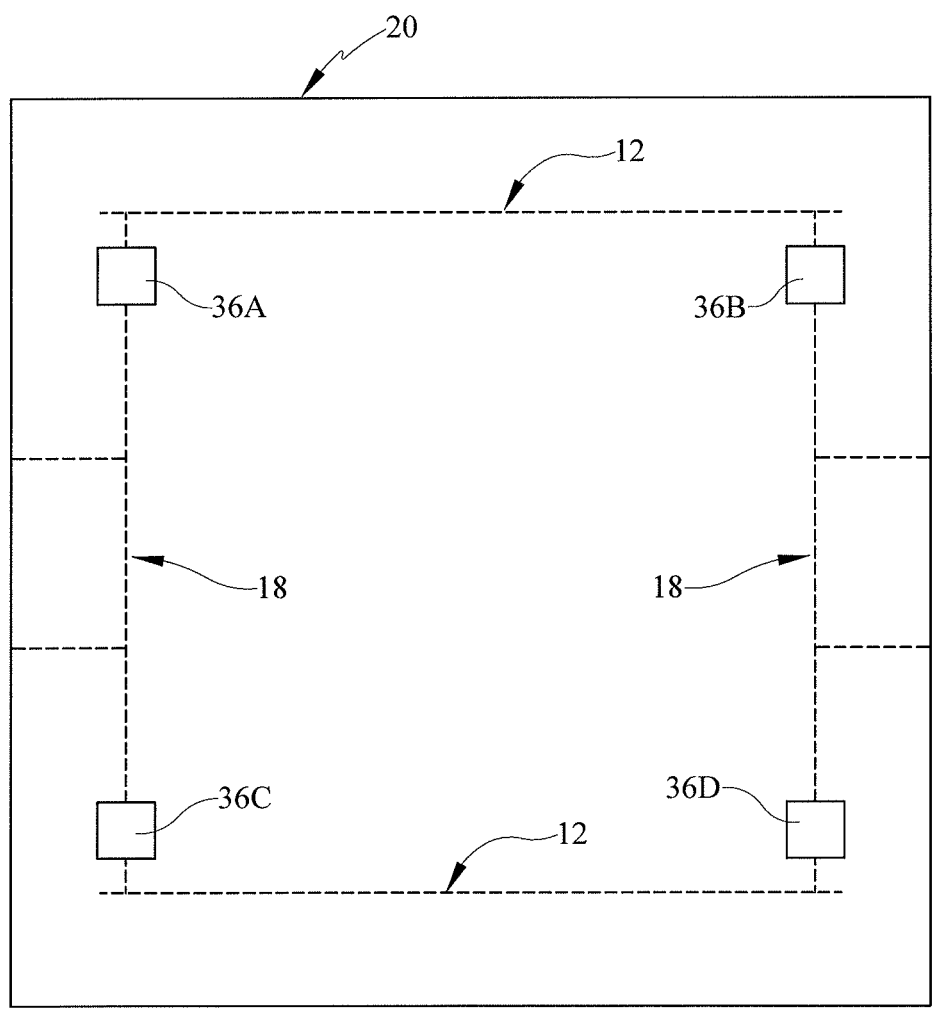
FIG. 2 is a block diagram illustrating exemplary locations of a number of load cells relative to the person support apparatus of FIG. 1, constructed according to one or more of the principles disclosed herein.

FIG. 2 shows a block diagram illustrating exemplary locations of a number of load cells 36 relative to the person support apparatus 10 of FIG. 1. FIG. 2 shows four load cells 36A, 36B, 36C and 36D distributed between the weigh frame 18 and the lower frame 12 in this embodiment. In other embodiments any number of load cells 36 may be used. In this embodiment the load path for the patient's weight is from the deck section 20 to the weigh frame 28 to the load cells 36 A-D to the lower frame 12. The lower frame 12 transmits the load to a supporting surface such as the ground.

Figure 3:
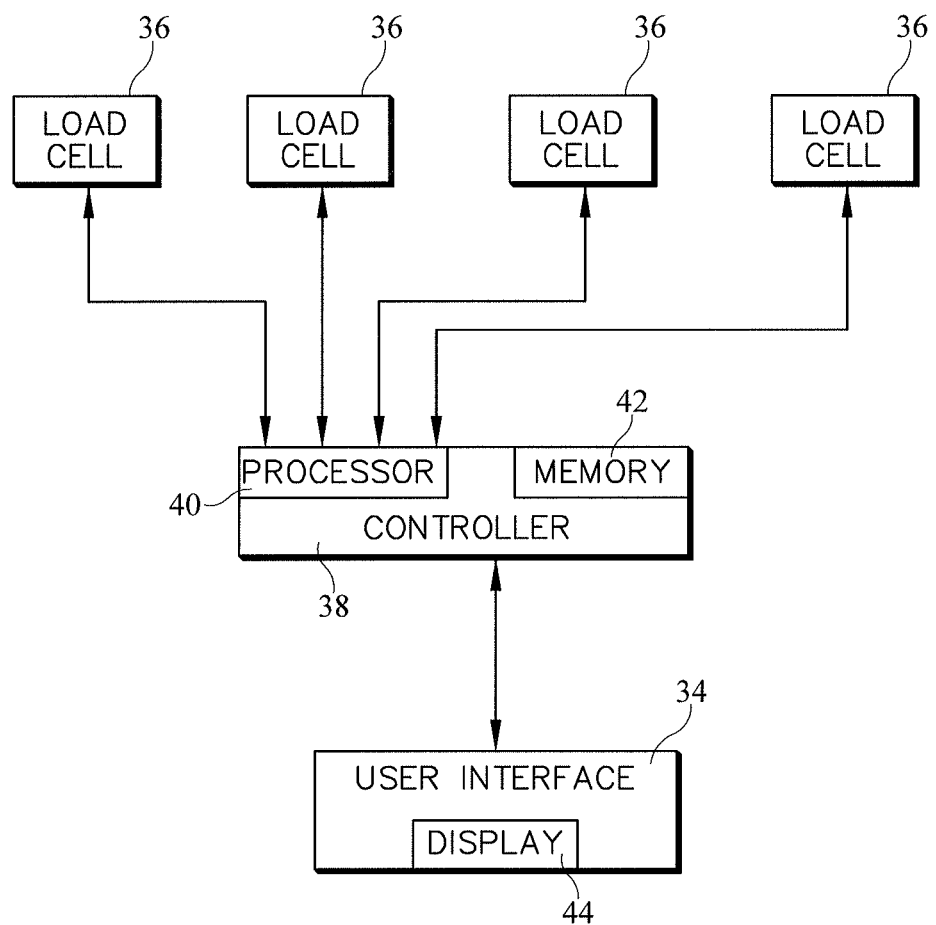
FIG. 3 is a block diagram illustrating one embodiment of a physiological sensing system, constructed according to one or more of the principles disclosed herein.

FIG. 3 is a block diagram showing some elements of one embodiment of physiological sensing system for use with a person support apparatus 10. Several load cells 36 are configured to communicate a signal indicative of the force experienced by them to a controller 38. In this embodiment the load cells 36 are configured to generate an electrical signal, while in other embodiments the load cells 36 may generate any type of signal including but not limited to optical signals. The controller 38 comprises at least one processor 40 and memory 42 in this embodiment. The processor 40 processes signals received from the load cells 36 in this embodiment while the memory 42 is configured to store at least one of the raw signals from the load cells 36 and/or the processed signals received from the processor 40.

In this embodiment the processor 40 and memory 42 are mounted on a circuit board (not shown). In one embodiment processor 40 comprises multiple processing units while in another embodiment the controller 38 comprises multiple processors and/or memory devices 42. Memory 42 may be of any type, including volatile and non-volatile memory. In this embodiment the controller 38 is configured to control at least one function of the person support apparatus, including but not limited to inflation and deflation of bladders, inclining and declining the head support deck section and raising and lowering the deck support section relative to the lower frame. In another embodiment the controller 38 is dedicated to processing signals from the load cells 36.

The controller 38 is configured to communicate with a user interface 34. In this embodiment the user interface comprises a touch screen display 44. The touch screen display 44 is configured to display system messages and alerts relayed to the user interface 34 by the controller 38. The user interface 34 is also configured to allow a caregiver and/or user to access functionality of the controller 38, including but not limited to activating and terminating the routine for physiological sensing. In this embodiment all connections are contemplated to be wired connections. In other embodiments connections between any one of the load cell 36 and the controller 38 and/or between the controller 38 and the user interface 34 is wireless.

Figure 4:
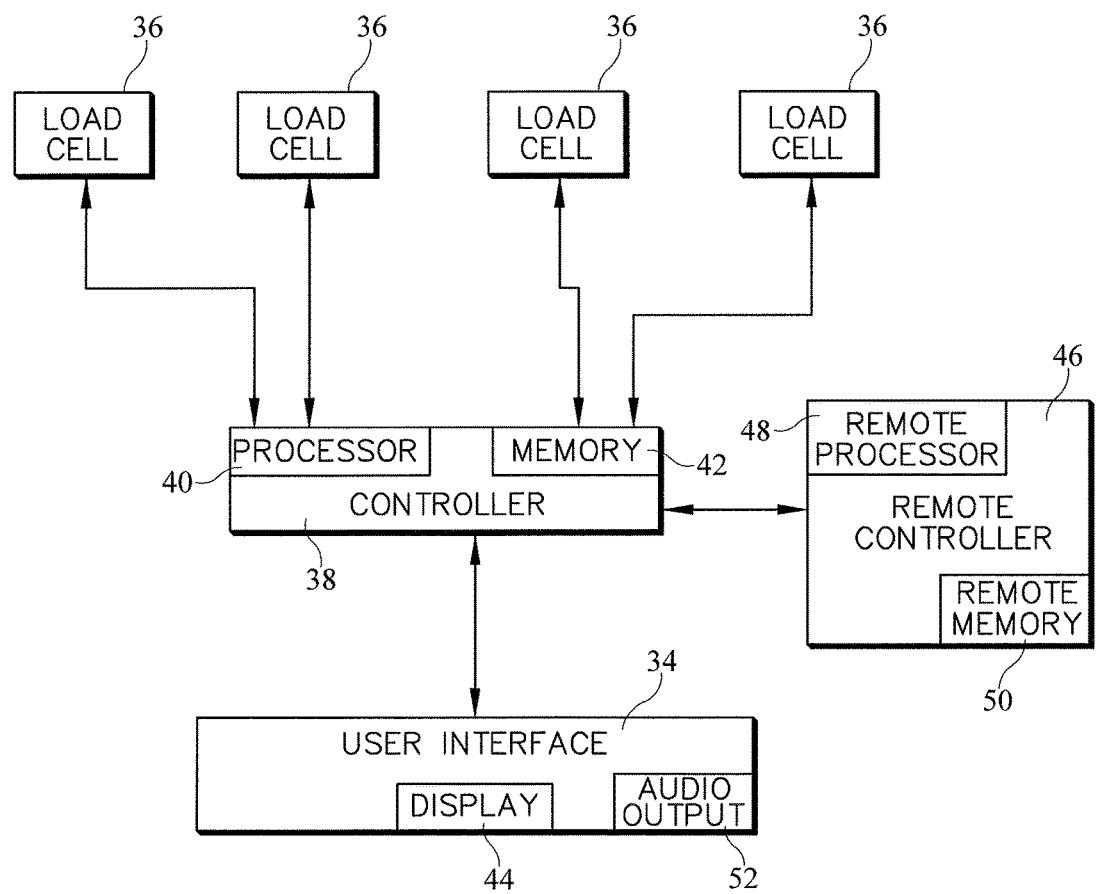
FIG. 4 is a block diagram illustrating another embodiment of a physiological sensing system, constructed according to one or more of the principles disclosed herein.

FIG. 4 is a block diagram showing some elements of one embodiment of physiological sensing system for use with a person support apparatus 10. Several load cells 36 are configured to communicate a signal indicative of the force experienced by them to a controller 38. In this embodiment the load cells 36 are configured to generate an electrical signal, while in other embodiments the load cells 36 may generate any type of signal including but not limited to optical signals. The controller 38 comprises at least one processor 40 and memory 42 in this embodiment. The processor 40 processes signals received from the load cells 36 in this embodiment while the memory 42 is configured to store at least one of the raw signals from the load cells 36 and/or the processed signals received from the processor 40. In this embodiment the processor 40 and memory 42 are mounted on a circuit board (not shown).

In one embodiment processor 40 comprises multiple processing units while in another embodiment the controller 38 comprises multiple processors and/or memory devices 42. Memory 42 may be of any type, including volatile and non-volatile memory. In this embodiment the controller 38 is configured to control at least one function of the person support apparatus, including but not limited to inflation and deflation of bladders (not shown) in the mattress 28, inclining and declining the head support deck section and raising and lowering the deck section 20 relative to the lower frame 12. In another embodiment the controller 38 is dedicated to processing signals from the load cells 36. Controller 38 is configured to communicate with a remote controller 46, remote controller 46 comprising at least one remote processor 48 and at least one remote memory 50. In one embodiment controller 38 is configured to communicate at least one of the raw signals from the load cells 36 and/or the processed signals to the remote controller 46. The remote controller 46 is configured to aid in the processing operation of the signals received from the load cells 36.

In this embodiment controller 38 partially processes signals received from the load cells 36 while the remote controller 46 completes processing. The remote controller 46 returns processed information to the controller 38 in this embodiment while in another embodiment the remote controller 46 communicates with a user interface 34. The remote memory 50 is configured to store at least one of the raw signals from the load cells 36 and/or the processed signals received from the processor 40 and processed signals received from remote processor 48. In this embodiment the remote controller 46 is configured to be a server located outside the hospital room housing the person support apparatus 10 while in other embodiments the remote controller 46 may be any device physically distinct from controller 38 located external or internal to the same hospital room as the person support apparatus 10 with the controller 38.

The controller 38 is configured to communicate with a user interface 34 in one embodiment. In this embodiment the user interface comprises a touch screen display 44 and an audio output 52. The touch screen display 44 is configured to display system messages and alerts relayed to the user interface 34 by the controller 38. The audio output is configured to produce an audible signal indicative of an alerting signal received from the controller 38. The user interface 34 is also configured to allow a caregiver and/or user to access functionality of the controller 38, including but not limited to activating and terminating the routine for physiological sensing. In this embodiment all connections are contemplated to be wired connections. In other embodiments connections between any one of the load cell 36 and the controller 38 and/or between the controller 38 and the user interface 34 and/or between the remote controller 46 and the controller 38 is wireless.

Figure 5:
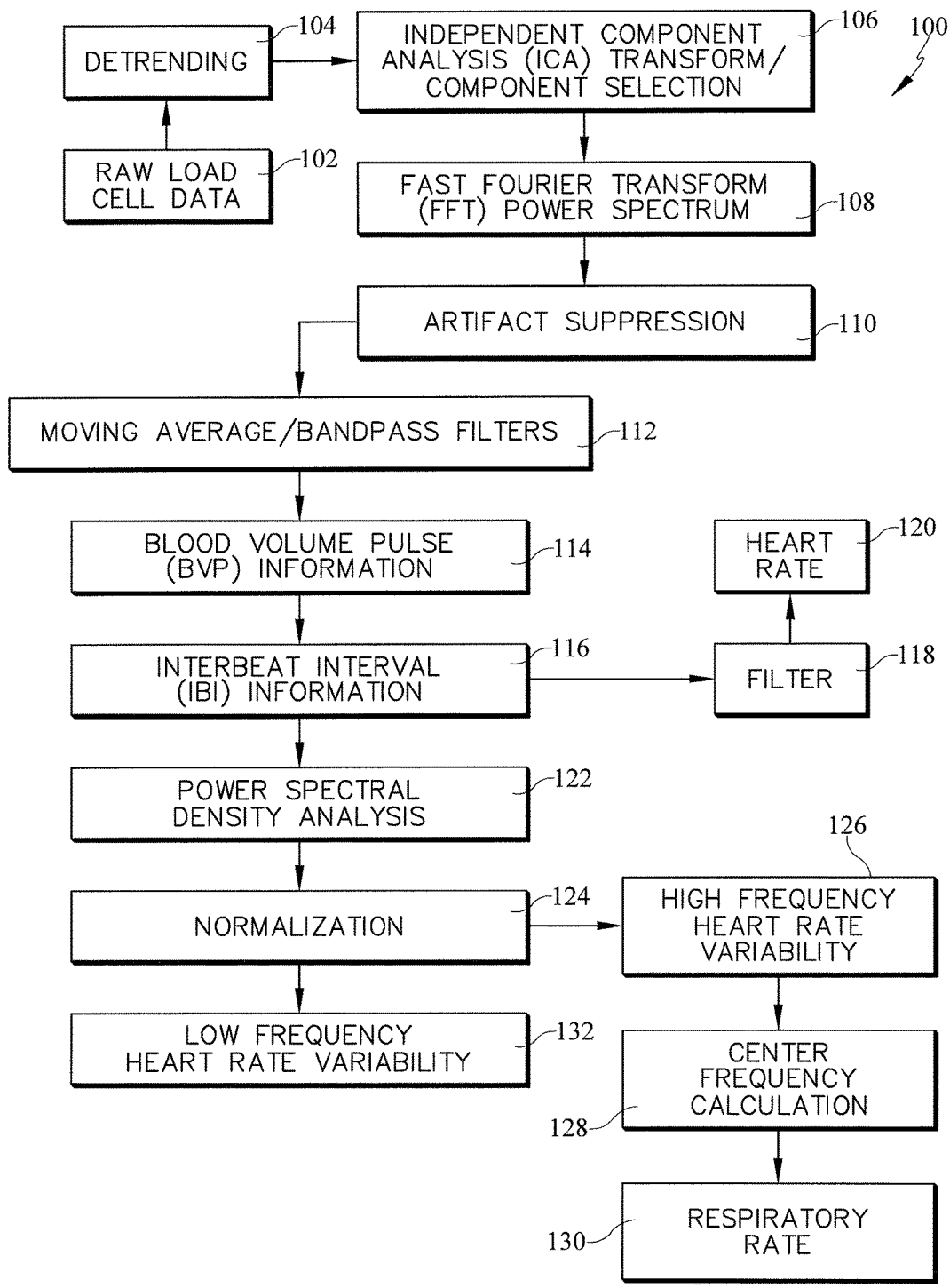
FIG. 5 is a flow chart illustrating a method of sensing physiological signals, constructed according to one or more of the principles disclosed herein.

FIG. 5 shows a flow chart 100 illustrating a method of sensing at least one physiological parameter using signals received from load cells 36. Any of the operations described below may be omitted and/or performed in sequences other than the exemplary embodiments described below, such permutations are contemplated to be part of this disclosure. Additional operations may be performed, including but not limited to transmission of data to an electronic healthcare database, data manipulating including smoothing and trending, alerting appropriate caregivers and charting and visualization of data are also contemplated to be part of this disclosure.

Flow chart 100 shows operation 102 wherein signals from at least two load cells 36 are collected. In this embodiment load cell data is collected at a rate of 15 Hz, while in other embodiments the load cell data may be collected at any rate. Load cell data is then processed to remove offset and/or gain errors and/or for trending artifacts in the data (in one exemplary embodiment, smoothing of data) in operation 104. In this embodiment the output of the load cell data that has undergone detrending in operation 104 is a 24 bit signal, while in other embodiments the signal may be of any size and frequency. In this embodiment detrending in operation 104 is accomplished through normalization based on a smoothness priors approach as shown in equation 1 below. In Equation 1 below, $y_i(t)$ is the raw load cell signal, $\mu_i$ and $\Omega_i$ are the mean and standard deviation of signal $y_i(t)$ respectively and $y_i'(t)$ is the normalized signal for each source of signal $i=1, 2, 3, \ldots, n$.

$$y_i'(t) = \frac{y_i(t) - \mu_i}{\sigma_i} \quad \text{Equation 1}$$

In another embodiment, any other method of normalizing load cell data may be used. In yet another embodiment raw load cell data may be used for blind source separation in operation 106 and operation 104 is not performed.

In operation 106, a blind source separation operation is performed, in this embodiment using independent component analysis (ICA) transform. ICA is one technique for separation of independent signals from a set of observations that are composed of linear mixtures of underlying source signals. The underlying signal of interest in this embodiment is the blood volume pulse information (BVP) that propagates through the body. During the cardiac cycle, increased flow through the body's blood vessels results in forces produced by the body on to objects in contact or in proximity to the body. As the BVP changes, each load cell of the bed records a mixture of the BVP signal with different weights. These observed signals are denoted by $y_1'(t), y_2'(t), \ldots, y_n'(t)$ which are signals recorded at time t. In this embodiment the ICA model assumes that the observed signals are linear mixes of the source signals as shown in equation 2 below. In equation 2 below y'(t) represents a matrix of observed signals, x(t) is an estimate of the underlying source signals and matrix A contains mixture coefficients.

$$y'(t) = Ax(t) \quad \text{Equation 2}$$

The object of ICA in this embodiment is to determine a demixing matrix W shown in equation 3 below that is an approximation of the inverse of the original mixing matrix A whose output is an estimate of the matrix x(t) containing the underlying source signals. In one embodiment iterative methods are used to maximize or minimize a cost function that measures the non-Gaussianity of each source to uncover the independent sources. In this embodiment ICA analysis is based on the Joint Approximation Diagonalization of Eigenmatrices (JADE) algorithm.

$$\hat{x}(t) = Wy'(t) \qquad \text{Equation 3}$$

Blind source separation ICA analysis in operation 106 is configured to separate from the load cell signals fluctuations caused predominantly by BVP. In one embodiment data received from load cells 36 includes operation of the mattress 28 and/or person support apparatus 10 including but not limited to percussion and vibration therapy and/or inflation and deflation of the mattress 28 and/or operation of any motors on the person support apparatus 10 and blind source separation ICA analysis is configured to separate these source signals. In one alternate embodiment identification of components of signals indicative of operation of the mattress 28 and/or person support apparatus 10 is aided by predetermined information identifying characteristics of operation of the mattress and/or person support apparatus 10.

Once the ICA signals are generated from operation 106, the function responsible for BVP is uncovered in operation 108 upon generation of power spectrums for the ICA signals. In one embodiment the power spectrum of the signal with the highest peak is selected for analysis. In another embodiment the signal with a peak in power spectrum in the range where BVP is known to exist is selected, this is done automatically in this embodiment, however in other embodiments a caregiver may select a signal of interest using user interface 34. In one embodiment, weight determined by the load cells is used to determine if a patient is indeed in bed. If it is determined that a person is not is bed, the operation is terminated and a message displayed to the caregiver in another embodiment.

The signal of interest identified in operation 108 undergoes an artifact suppression process in operation 110 in this embodiment. The artifact suppression operation in this embodiment includes interpolation and/or removal of data while in another embodiment data may be normalized after interpolation and/or removal. In yet another embodiment operation 108 of artifact suppression may be omitted.

In operation 112 the signal of interest is smoothed. In this embodiment the signal of interest is smoothed using a five point moving average filter and bandpass filtered in an area of interest, in this embodiment 0.7-4 Hz. In other embodiments any data manipulation algorithm may be used.

Blood volume pulse information is obtained in operation 114 which is further refined. In this embodiment the BVP peak fiducial point is refined by interpolating the signal with a cubic spline function at a frequency of 256 Hz. In other embodiments any other data processing function may be performed.

Interbeat interval information (IBI) is determined from BVP information in operation 116. The IBI signal is filtered in operation 118 to determine the Heart Rate (HR) information in operation 120. In this embodiment the IBI signal is filtered using the noncausal of variable threshold (NC-VT) algorithm in operation 118. Heart Rate (HR) is calculated from the mean IBI time series as 60/IBI in this embodiment. In this embodiment heart rate information is displayed on the display 44. In one embodiment if the heart rate information falls outside a predetermined range an alerting message is displayed on the display 44 in one embodiment, and an audio alert is sounded via the audio output 52 in another embodiment. In one embodiment the alerting message is transmitted to a remote display and/or audio output and/or caregiver station and/or nurse call system by wired or wireless connections. In one embodiment heart rate is expressed as beats per minute (bpm).

In operation 122 power spectral density estimation analysis of IBI information is used to identify heat rate variability (HRV) information. In this embodiment Lomb periodogram is used to analyze HRV. Information from power spectral density estimation analysis is normalized in operation 124 in this embodiment, while in other embodiments this operation may be eliminated. Normalized information from operation 124 is analyzed in operation 132 for analyzing baroflex activity. In this embodiment low frequency heart rate variability component in the 0.04-0.15 Hz range is analyzed in operation 132 for baroflex activity which is modulated by sympathetic and/or parasympathetic influences.

Normalized information from operation 124 is analyzed in operation 126 for analyzing respiratory rate. In this embodiment high frequency component of the heart rate variability information in the 0.15-0.40 Hz range is analyzed. The high frequency component reflects parasympathetic influence on the heart through efferent vagal activity and could be connected to Respiratory Sinus Arrhythmia (RSA), a cardiorespiratory phenomenon characterized by IBI fluctuations that are in phase with inhalation and exhalation. The ratio of low frequency heart rate variability to high frequency heart rate variability is considered to mirror sympatho/vagal balance or to reflect sympathetic modulations. In operation 128 center frequency of the peak in the high frequency heart rate variability ($f_{HI\_Fpeak}$) information is determined. Respiratory rate is determined as $60/f_{HI\_Fpeak}$ in operation 130. When the frequency of respiration changes, the center frequency of the high frequency component of the heart rate variability shifts. In one embodiment respiratory rate is expressed as breaths per minute.

In one embodiment respiratory rate and/or portions of heart rate variability information and/or heat rate is displayed on the display 44. In one embodiment if at least one of respiratory rate, or portions of heart rate variability information and/or heat rate fall outside a predetermined range an alerting message is displayed on display 44 and/or an audio alert is sounded via the audio output 52 in another embodiment. In one embodiment the alerting message is transmitted to a remote display and/or audio output and/or caregiver station and/or nurse call system by wired or wireless connections.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Preferred embodiments are described herein, including the best mode known to the inventor for carrying out the claimed subject matter. Of course, variations of those preferred embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

The disclosures of any references and publications cited above are expressly incorporated by reference in their entireties to the same extent as if each were incorporated by reference individually.

The invention claimed is:

1. A system comprising:
   a person support apparatus embodied as a hospital bed comprising a lower frame supported on wheels, a weigh frame supported by supports for variable elevation relative to the lower frame, at least one deck section supported on the weigh frame, and a set of siderails movable with respect to the weigh frame and the at least one deck section between raised and lowered positions;
   at least two force transducers configured to mount on said person support apparatus, said at least two force transducers configured to generate signals indicative of forces acting on said at least two force transducers by a person supported on the hospital bed; and
   a controller carried by the hospital bed and comprising a processor configured to receive signals from said at least two force transducers, said controller configured to process the signals received from said at least two force transducers to determine the person's weight and to determine blood volume pulse based only on the signals from said at least two force transducers by causing the signals to undergo blind source separation analysis including an independent component analysis (ICA) transform to identify source signals indicative of forces produced by the person onto the hospital bed, the source signals being indicative of varying flow through the person's blood vessels during the person's cardiac cycle, wherein after the ICA transform the controller performs artifact suppression on the source signals, wherein the controller is also operable to control movement of the at least one deck section and weigh frame relative to the lower frame, wherein each force transducer of the at least two force transducers detects a mixture of the blood volume pulse and the person's weight, wherein weight detected by the at least two force transducers is used by the controller to determine if the person is supported on the hospital bed and, if it is determined by the controller that the person is not supported on the hospital bed, the operation to determine blood volume pulse is terminated and a message displayed on a touch screen display of the hospital bed.

2. The system of claim 1, further comprising a memory wherein said memory is configured to store at least one of signals received from said at least two force transducers and processed signals.

3. The system of claim 1, further comprising a remote controller comprising a remote processor, said remote controller in communication with said controller.

4. The system of claim 1, further comprising a user interface in communication with said controller, said user interface comprising a display configured to display messages received from said controller.

5. The system of claim 4, wherein said user interface further comprises an audio output configured to output an audio signal.

6. The system of claim 1, wherein said controller is configured to determine heart rate from said blood volume pulse.

7. The system of claim 1, wherein said controller is configured to determine respiratory rate from said blood volume pulse.

8. A person support apparatus embodied as a hospital bed comprising:
   a lower frame supported on wheels;
   a weigh frame supported by supports for variable elevation relative to the lower frame;
   at least one deck section supported on the weigh frame;
   a set of siderails movable with respect to the weigh frame and the at least one deck section between raised and lowered positions;
   a mattress supported by the at least one deck section and configured to support a person;
   at least two force transducers configured to generate signals indicative of components of weight of a person supported by said mattress acting on said at least two force transducers; and
   a controller carried by the hospital bed and comprising a processor configured to receive signals from said at least two force transducers, said controller configured to process the signals received from said at least two force transducers to determine the person's weight and to determine blood volume pulse based only on the signals from said at least two force transducers by causing the signals to undergo blind source separation analysis including an independent component analysis (ICA) transform to identify source signals indicative of forces produced by the person onto the hospital bed, the source signals being indicative of varying flow through the person's blood vessels during the person's cardiac cycle, wherein after the ICA transform the controller performs artifact suppression on the source signals, wherein the controller is also operable to control movement of the at least one deck section and weigh frame relative to the lower frame, wherein each force transducer of the at least two force transducers detects a mixture of the blood volume pulse and the person's weight, wherein weight detected by the at least two force transducers is used by the controller to determine if the person is supported on the hospital bed and, if it is determined by the controller that the person is not supported on the hospital bed, the operation to determine blood volume pulse is terminated and a message displayed on a touch screen display of the hospital bed.

9. The person support apparatus of claim 8, further comprising a remote controller comprising a remote processor, said remote controller in communication with said controller.

10. The person support apparatus of claim 8, further comprising a user interface in communication with said controller, said user interface comprising a display configured to display information received from said controller.

11. The person support apparatus of claim 8, wherein said controller is configured to determine heart rate from said blood volume pulse.

12. The person support apparatus of claim 8, wherein said controller is configured to determine respiratory rate from said blood volume pulse.

13. A physiological signal sensing system for use with a person support apparatus embodied as a hospital bed comprising a lower frame supported on wheels, a weigh frame supported by supports for variable elevation relative to the lower frame, at least one deck section supported on the weigh frame, and a set of siderails movable with respect to the weigh frame and the at least one deck section between raised and lowered positions, the system comprising:
   at least two force transducers configured to generate signals in response to a person's weight supported by said at least two force transducers; and
   a controller carried by the hospital bed and comprising a processor configured to receive signals from said at least two force transducers, said controller configured to process the signals received from said at least two force transducers to determine the person's weight to determine blood volume pulse based only on the signals from said at least two force transducers by causing the signals to undergo blind source separation analysis including an independent component analysis (ICA) transform to identify source signals indicative of forces produced by the person onto the hospital bed, the source signals being indicative of varying flow through the person's blood vessels during the person's cardiac cycle, wherein after the ICA transform the controller performs artifact suppression on the source signals, wherein the controller is also operable to control movement of the at least one deck section and weigh frame relative to the lower frame, wherein each force transducer of the at least two force transducers detects a mixture of the blood volume pulse and the person's weight, wherein weight detected by the at least two force transducers is used by the controller to determine if the person is supported on the hospital bed and, if it is determined by the controller that the person is not supported on the hospital bed, the operation to determine blood volume pulse is terminated and a message displayed on a touch screen display of the hospital bed.

14. The system of claim 13, wherein said controller is configured to determine heart rate from said blood volume pulse.

15. The system of claim 14, further comprising a display device configured to display heart rate.

16. The system of claim 13, wherein said controller is configured to determine respiratory rate from said blood volume pulse.

17. The system of claim 16, further comprising a display device configured to display respiratory rate information.

18. A system comprising:
   a person support apparatus embodied as a hospital bed comprising a lower frame supported on wheels, a weigh frame supported by supports for variable elevation relative to the lower frame, at least one deck section supported on the weigh frame, and a set of siderails movable with respect to the weigh frame and the at least one deck section between raised and lowered positions;
   means to generate signals indicative of components of weight acting said person support apparatus by a person; and
   means carried by the hospital bed to determine blood volume pulse from said signals indicative of components of weight acting on said person support apparatus based only on the signals from said means to generate signals by causing the signals to undergo blind source separation analysis including an independent component analysis (ICA) transform to identify source signals indicative of forces produced by the person onto the hospital bed, the source signals being indicative of varying flow through the person's blood vessels during the person's cardiac cycle, wherein the controller is also operable to control movement of the at least one deck section and weigh frame relative to the lower frame, wherein after the ICA transform the means to determine blood volume pulse performs artifact suppression on the source signals, wherein the means to generate signals detects a mixture of the blood volume pulse and the person's weight, wherein weight detected by the means to generate signals is used by the means to determine blood volume pulse to determine if the person is supported on the hospital bed and, if it is determined by the means to determine blood volume pulse that the person is not supported on the hospital bed, the operation to determine blood volume pulse is terminated and a message displayed on a touch screen display of the hospital bed.

19. The system of claim 18, further comprising means to display heart rate derived from said blood volume pulse.

20. The system of claim 18, further comprising means to display respiratory rate derived from said blood volume pulse.

21. A method of sensing a physiological signal of a person supported by a person support apparatus embodied as a hospital bed comprising a lower frame supported on wheels, a weigh frame supported by supports for variable elevation relative to the lower frame, at least one deck section supported on the weigh frame, and a set of siderails movable with respect to the weigh frame and the at least one deck section between raised and lowered positions, the method comprising:
   generating signals indicative of components of forces acting on said person support apparatus by a person using at least two force transducers;
   transmitting said signals to a controller carried by the hospital bed; and
   with the controller, processing signals indicative of components of forces acting on said person support apparatus to determine blood volume pulse based only on the signals from said at least two force transducers by causing the signals to undergo blind source separation analysis including an independent component analysis (ICA) transform to identify source signals indicative of forces produced by the person onto the hospital bed, the source signals being indicative of varying flow through the person's blood vessels during the person's cardiac cycle, wherein after the ICA transform the controller performs artifact suppression on the source signals, wherein the controller is also operable to control movement of the at least one deck section and weigh frame relative to the lower frame, wherein each force transducer of the at least two force transducers detects a mixture of the blood volume pulse and the person's weight, wherein weight detected by the at least two force transducers is used by the controller to determine if the person is supported on the hospital bed and, if it is determined by the controller that the person is not supported on the hospital bed, the operation to determine blood volume pulse is terminated and a message displayed on a touch screen display of the hospital bed.

22. The method of claim 21, further comprising the operation of determining heart rate from said blood volume pulse.

23. The method of claim 22, further comprising the operation of displaying heart rate on a display device.

24. The method of claim 21, further comprising the operation of determining respiratory rate from said blood volume pulse.

25. The method of claim 24, further comprising the operation of displaying respiratory rate on a display device.

26. The method of claim 21, further comprising the operation of normalizing operation of at least one of a mattress supported by said person support apparatus and said person support apparatus.

\* \* \* \* \*